United States Patent
Nariyama et al.

(10) Patent No.: US 11,211,618 B2
(45) Date of Patent: Dec. 28, 2021

(54) FLOW BATTERY THAT INCLUDES LIQUID CONTAINING MEDIATOR

(71) Applicant: Panasonic Intellectual Property Management Co., Ltd., Osaka (JP)

(72) Inventors: Honami Nariyama, Osaka (JP); Yu Otsuka, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 234 days.

(21) Appl. No.: 16/005,451

(22) Filed: Jun. 11, 2018

(65) Prior Publication Data

US 2018/0366747 A1   Dec. 20, 2018

(30) Foreign Application Priority Data

Jun. 16, 2017  (JP) .............................. JP2017-119084

(51) Int. Cl.

| | |
|---|---|
| *H01M 8/04186* | (2016.01) |
| *H01M 8/18* | (2006.01) |
| *H01M 8/04082* | (2016.01) |
| *H01M 4/36* | (2006.01) |
| *C07D 339/08* | (2006.01) |
| *C07D 327/08* | (2006.01) |
| *C07D 319/24* | (2006.01) |
| *H01M 4/60* | (2006.01) |

(52) U.S. Cl.
CPC ...... *H01M 8/04186* (2013.01); *C07D 319/24* (2013.01); *C07D 327/08* (2013.01); *C07D 339/08* (2013.01); *H01M 4/368* (2013.01); *H01M 4/60* (2013.01); *H01M 8/04201* (2013.01); *H01M 8/188* (2013.01); *H01M 2300/0025* (2013.01)

(58) Field of Classification Search
CPC .... H01M 8/04186; H01M 4/368; H01M 4/60; H01M 8/04201; H01M 8/188; C07D 319/24; C07D 3247/08; C07D 339/08
See application file for complete search history.

(56) References Cited

U.S. PATENT DOCUMENTS

| | | | |
|---|---|---|---|
| 2014/0178735 A1 | 6/2014 | Wang et al. | |
| 2017/0062842 A1* | 3/2017 | Huang | ................. C07D 279/22 |
| 2018/0048004 A1 | 2/2018 | Hojo | |

FOREIGN PATENT DOCUMENTS

| | | | | |
|---|---|---|---|---|
| JP | 2010-085570 | 4/2010 | | |
| JP | 2014-524124 | 9/2014 | | |
| JP | 2016-103386 | 6/2016 | | |
| WO | WO-2013131838 A1 * | 9/2013 | .......... | H01M 4/8631 |
| WO | 2016/208123 | 12/2016 | | |

\* cited by examiner

*Primary Examiner* — Helen Oi K Conley
(74) *Attorney, Agent, or Firm* — Renner, Otto, Boisselle & Sklar, LLP (57) ABSTRACT

A flow battery includes a first liquid containing a redox mediator, a first electrode, a first active material, and a first circulator that circulates the first liquid between the first electrode and the first active material. The redox mediator contains a heteranthrene compound. The redox mediator contains a heteranthrene compound. The heteranthrene compound has a skeletal structure including a central ring structure, the central ring structure containing no nitrogen.

16 Claims, 4 Drawing Sheets

FLOW BATTERY THAT INCLUDES LIQUID CONTAINING MEDIATOR

BACKGROUND

1. Technical Field

The present disclosure relates to a flow battery that includes a liquid containing a mediator.

2. Description of the Related Art

Japanese Unexamined Patent Application Publication (Translation of PCT Application) No. 2014-524124 discloses a redox flow battery system that includes an energy storage containing a redox mediator. International Publication No. WO 2016/208123 discloses a flow battery containing a redox species.

SUMMARY

It is desirable that a flow battery contains a solid positive-electrode active material with a high electric potential in order to have a high discharge potential.

In one general aspect, the techniques disclosed here feature a flow battery that includes a first liquid containing a redox mediator, a first electrode, a first active material, and a first circulator that circulates the first liquid between the first electrode and the first active material. The redox mediator contains a heteranthrene compound. The heteranthrene compound has a skeletal structure including a central ring structure, the central ring structure containing no nitrogen.

An embodiment of the present disclosure can provide a flow battery containing a positive-electrode active material with a high electric potential.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Embodiments of the present disclosure will be described below with reference to the accompanying drawings.

First Embodiment

Figure 1:
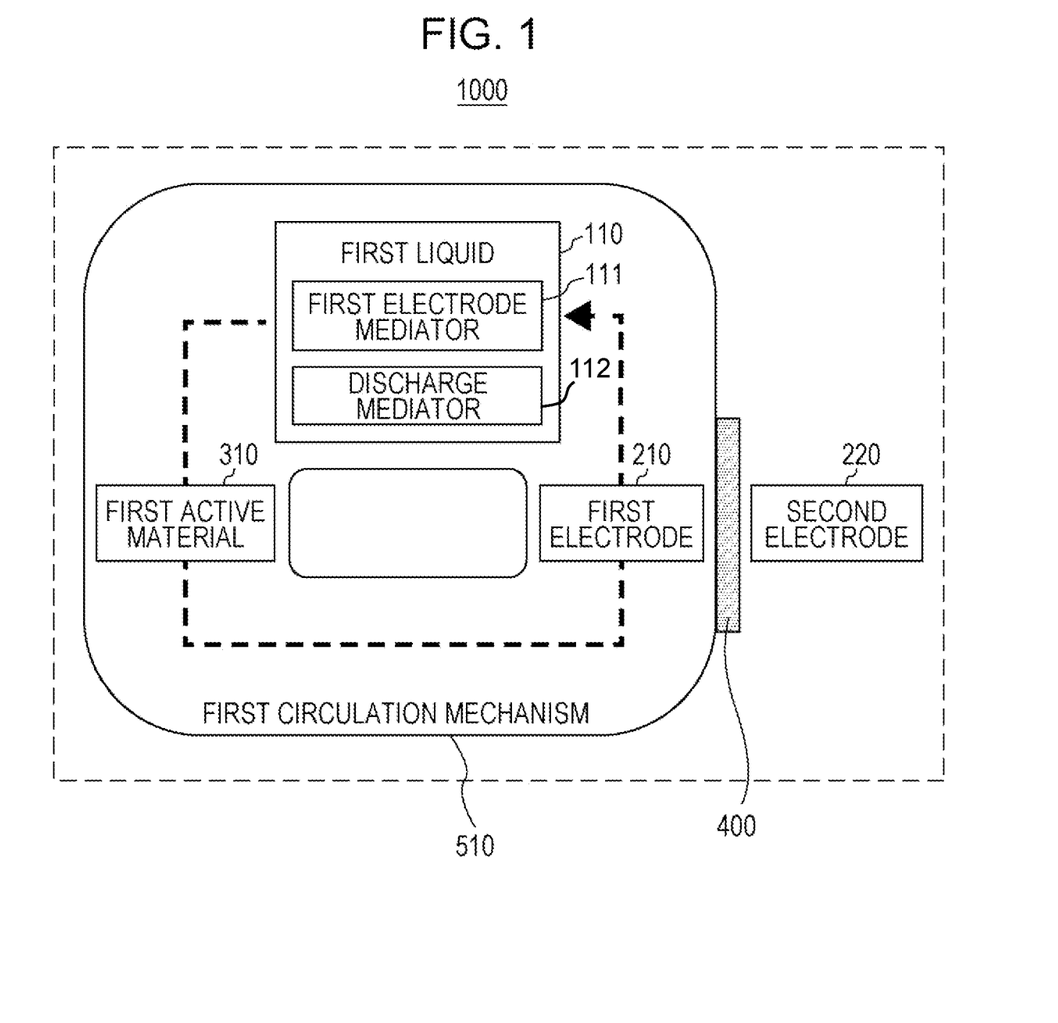
FIG. 1 is a schematic block diagram of a flow battery according to a first embodiment.

FIG. 1 is a schematic block diagram of a flow battery 1000 according to a first embodiment.

The flow battery 1000 according to the first embodiment includes a first liquid 110, a first electrode 210, a first active material 310, and a first circulator (hereinafter referred to as first circulation mechanism) 510.

The first liquid 110 contains a first electrode mediator (an example of a redox mediator) 111 dissolved therein.

The first electrode 210 is immersed in the first liquid 110.

The first active material 310 is immersed in the first liquid 110.

The first circulation mechanism 510 circulates the first liquid 110 between the first electrode 210 and the first active material 310.

The first electrode mediator 111 contains a heteranthrene compound.

The heteranthrene compound 111 has a skeletal structure including a central ring structure, the central ring structure containing no nitrogen.

Such a structure can improve the discharge potential, energy density, and cycle life of a flow battery. In such a structure, a heteranthrene compound, which has a redox potential of approximately 4 V, can be used as a charge mediator for $LiCoO_2$, $LiNiO_2$, or $LiMn_2O_4$ and as a discharge mediator for $LiNi_{0.5}Mn_{1.5}O_4$. A heteranthrene compound may be used alone. This allows an active material with a high equilibrium potential to be used as the first active material 310 and can thereby increase the discharge potential of a flow battery. The active material with a high equilibrium potential may have a potential in the range of approximately 3.8 to 4.5 V vs. $Li/Li^+$.

Furthermore, such a structure can utilize an active material for a flow battery without circulating the active material. Thus, a high-capacity active material powder can be used as the first active material 310 in a charge-discharge reaction, for example. This can increase the energy density and capacity.

Such a structure can circulate only the first liquid 110 containing the first electrode mediator 111 dissolved therein without circulating an active material powder. This can reduce the occurrence of clogging of a pipe with the active material powder. Thus, the flow battery can have a long cycle life.

In the flow battery 1000 according to the first embodiment, the heteranthrene compound may be represented by the following general formula (1):

where $X_1$ and $X_2$ each independently denote at least one chalcogen element selected from the group consisting of S, O, Se, and Te,

$Y_1$ to $Y_8$ each independently denote hydrogen, fluorine, chlorine, bromine, a cyano group, a nitro group, a chain saturated hydrocarbon group, a chain unsaturated hydrocarbon group, a cyclic saturated hydrocarbon group, a cyclic unsaturated hydrocarbon group, $—COR_1$, or $—N(R_2)_2$, and $R_1$ and $R_2$ each independently denote at least one selected from the group consisting of hydrogen, a chain saturated hydrocarbon group, a chain unsaturated hydrocarbon group, a cyclic saturated hydrocarbon group, a cyclic unsaturated hydrocarbon group, a cyano group, a nitro group, and any combination thereof.

Such a structure enables the use of a solid positive-electrode active material with a high electric potential and can increase the discharge voltage of a flow battery. The chain saturated hydrocarbon group, the chain unsaturated hydrocarbon group, the cyclic saturated hydrocarbon group, and the cyclic unsaturated hydrocarbon group of any of $Y_1$ to $Y_8$ and $R_1$ and $R_2$ may each independently contain at least one selected from the group consisting of an oxygen atom, a nitrogen atom, a sulfur atom, and a silicon atom.

In such a structure, an electron-donating conjugation effect due to the presence of an unshared electron pair of a chalcogen element at positions 1 and 4 can stabilize a cation radical of the heteranthrene compound, thereby allowing reversible charge-discharge and increasing the discharge potential of the flow battery.

In the flow battery 1000 according to the first embodiment, the heteranthrene compound may be represented by the following general formula (2):

(2)

wherein $X_1$ and $X_2$ each independently denote at least one chalcogen element selected from the group consisting of S, O, Se, and Te.

Such a structure can increase the discharge potential of a flow battery.

In the flow battery 1000 according to the first embodiment, $Y_1$ to $Y_8$ in a heteranthrene compound represented by the general formula (1), each independently denote hydrogen, fluorine, chlorine, bromine, a cyano group, a nitro group, a chain saturated hydrocarbon group, a chain unsaturated hydrocarbon group, a cyclic saturated hydrocarbon group, a cyclic unsaturated hydrocarbon group, —$COR_1$, or —$N(R_2)_2$. $R_1$ and $R_2$ each independently denote at least one selected from the group consisting of hydrogen, a chain saturated hydrocarbon group, a chain unsaturated hydrocarbon group, a cyclic saturated hydrocarbon group, a cyclic unsaturated hydrocarbon group, a cyano group, a nitro group, and any combination thereof. $R_1$ and $R_2$ may each independently include at least one element (non-metallic element) selected from the group consisting of boron, nitrogen, oxygen, fluorine, silicon, phosphorus, sulfur, chlorine, bromine, and iodine. The chain saturated hydrocarbon group may have 1 to 10 carbon atoms. Examples of the chain saturated hydrocarbon group having 1 to 10 carbon atoms include a methyl group, an ethyl group, a n-propyl group, an isopropyl group, a n-butyl group, a n-pentyl group, an isopentyl group, a neopentyl group, a n-hexyl group, a 2-methylpentyl group, a 3-methylpentyl group, a 2,3-dimethylhexyl group, a 2,2-dimethylbutyl group, a 2,3-dimethylbutyl group, a 2,2-dimethylpentyl group, a 2,3-dimethylpentyl group, a 2,2-dimethylhexyl group, a n-heptyl group, a n-octyl group, a n-nonyl group, and a n-decyl group. The straight-chain unsaturated hydrocarbon group may have 2 to 20 carbon atoms. Examples of the chain unsaturated hydrocarbon group include a vinyl group, an aryl group, a 1-butenyl group, a 2-butenyl group, a 1-heptenyl group, a 1-octenyl group, a 1-nonenyl group, and a 1-decenyl group. The cyclic saturated hydrocarbon group may have 3 to 20 carbon atoms. Examples of the cyclic saturated hydrocarbon group include a cyclopropyl group, a cyclobutyl group, a cyclopentyl group, a cyclohexyl group, a cycloheptyl group, a cyclooctyl group, a cyclononyl group, a cyclodecyl group, a methylcyclohexyl group, a methylcyclopentyl group, a dimethylcyclopentyl group, a 1-bicyclo[4.4.0]decyl group, and a 2-bicyclo[4.4.0]decyl group. The cyclic unsaturated hydrocarbon group may have 3 to 20 carbon atoms. Examples of the cyclic unsaturated hydrocarbon group include a cyclopentenyl group, a cyclohexenyl group, a cycloheptenyl group, a 4-methylcyclohexenyl group, and a 1-methylcyclohexenyl group.

Such a structure can increase the discharge potential of a flow battery.

In the flow battery 1000 according to the first embodiment, the heteranthrene compound may be at least one selected from the group consisting of thianthrene, phenoxathiin, and dibenzo[b,e][1,4]dioxin.

Such a structure can increase the discharge potential of a flow battery.

Table 1 lists the measured electric potentials of heteranthrene compounds usable as the first electrode mediator 111.

TABLE 1

| Compound name | Structural formula | Molecular weight | m.p. (° C.) | Electrolytic solution | Electric potential [V vs. Li/Li+] | | | |
|---|---|---|---|---|---|---|---|---|
| | | | | | $E_1$ox | $E_1$red | $E_2$ox | $E_2$red |
| Thianthrene | | 216.32 | 155.0-159.0 | $LiBF_4$/PC | 4.09 | 4.01 | 4.6 | 4.51 |
| Phenoxathiin | | 200.26 | 55-58 | $LiPF_6$/FEC | 3.88 | 3.8 | 4.65 | 4.57 |
| Dibenzo[b,e][1,4]dioxin | | 184.19 | — | $LiBF_4$/PC | 4.34 | 4.25 | — | — |

An electrolytic solution of 1 M electrolyte dissolved in a solvent was prepared. The electrolyte was $LiBF_4$ or $LiPF_6$. The solvent was propylene carbonate (PC) or fluoroethylene carbonate (FEC). Table 1 lists combinations of electrolyte and solvent. 5 mM of each heteranthrene compound listed in Table 1 was dissolved in the electrolytic solution to prepare an electrolytic solution of the heteranthrene compound. An electrometric cell for each heteranthrene compound listed in Table 1 was fabricated from the electrolytic solution, a counter electrode, a working electrode, and a reference electrode. The counter electrode was a 1×1 cm² Pt foil. The working electrode was a glassy carbon electrode for electrochemical measurement (ϕ6 mm). The reference electrode was a silver wire ($Ag/Ag^+$). The electrometric cell was used to measure the charge-discharge potential of each heteranthrene compound listed in Table 1 by cyclic voltammetry (CV). Table 1 lists the measured charge-discharge potentials based on lithium metal (V vs. $Li/Li^+$).

Table 1 shows that the heteranthrene compounds have a redox potential in the range of 3.8 to 4.7 (V vs. $Li/Li^+$). Thus, such a heteranthrene compound can be used as a charge mediator for a solid positive-electrode active material with an equilibrium potential lower than the first oxidation potential, which is the charge potential. Such a heteranthrene compound can be used alone as a charge-discharge mediator for a solid positive-electrode active material with an equilibrium potential between the second oxidation potential and the first reduction potential, which is the discharge potential. More specifically, the oxidation potential in the second step (second oxidation potential: $E_2ox$ (V vs. $Li/Li^+$)) is the charge potential of the mediator, and the reduction potential in the first step (first reduction potential: $E_1red$ (V vs. $Li/Li^+$)) is the discharge potential of the mediator.

The heteranthrene compounds, thianthrene, phenoxathiin, and dibenzo[b,e][1,4]dioxin, have a first redox potential approximately 0.5 V higher than those of tetrathiafulvalenes or known positive-electrode discharge mediators.

The discharge potential of a flow battery depends on the electric potential of a positive-electrode discharge mediator. Thus, the heteranthrene compounds according to the first embodiment, which have a high discharge potential, can increase the discharge potential of a flow battery.

In the flow battery 1000 according to the first embodiment, the first electrode mediator 111 may contain only one heteranthrene compound according to the first embodiment.

In the flow battery 1000 according to the first embodiment, the first electrode mediator 111 may contain two or more of the heteranthrene compounds according to the first embodiment.

As described above, the heteranthrene compounds according to the first compound have a first oxidation potential $E_1ox$, a second oxidation potential $E_2ox$, a first reduction potential $E_1red$, and a second reduction potential $E_2red$.

The first active material 310 may have an equilibrium potential (V vs. $Li/Li^+$) lower than the first oxidation potential $E_1ox$ or second oxidation potential $E_2ox$ and higher than the first reduction potential $E_1red$ or second reduction potential $E_2red$.

In such a structure, the use of an active material with an equilibrium potential higher than the first reduction potential $E_1red$ or second reduction potential $E_2red$ as the first active material 310 allows a heteranthrene compound according to the first embodiment to function as a discharge mediator. In other words, the use of an active material with a lower potential than the first reduction potential $E_1red$ or second reduction potential $E_2red$ as the first active material 310 allows a heteranthrene compound according to the first embodiment to function as a discharge mediator. On the other hand, the use of an active material with an equilibrium potential lower than the first oxidation potential $E_1ox$ or second oxidation potential $E_2ox$ as the first active material 310 allows a heteranthrene compound according to the first embodiment to function as a charge mediator. In other words, the use of an active material with a lower potential than the first oxidation potential $E_1ox$ or second oxidation potential $E_2ox$ as the first active material 310 allows a heteranthrene compound according to the first embodiment to function as a charge mediator.

In the flow battery 1000 according to the first embodiment, the first active material 310 may be a metal oxide represented by $Li_xM_yO_2$. M denotes at least one selected from the group consisting of Ni, Mn, and Co. The variables x and y may be any number. The metal oxide has an equilibrium potential in the range of 3.8 to 4.4 V.

In the flow battery 1000 according to the first embodiment, the first active material 310 may be at least one selected from the group consisting of $LiFePO_4$, $LiMnO_2$, $LiMn_2O_4$, and $LiCoO_2$.

$LiCoO_2$ has an equilibrium potential of 3.9 V vs. $Li/Li^+$. Thus, a mediator-type positive electrode containing $LiCoO_2$ as an active material can be formed by using a compound with a discharge potential higher than the equilibrium potential of $LiCoO_2$ and with a charge potential lower than the equilibrium potential of $LiCoO_2$ as the first electrode mediator 111, which is the charge-discharge mediator. In this case, a smaller potential difference between the equilibrium potential of $LiCoO_2$ and the charge-discharge potential of the first electrode mediator 111 results in higher charge-discharge energy efficiency. For example, a discharge potential of the first electrode mediator 111 lower than the equilibrium potential of $LiCoO_2$ and closer to the equilibrium potential of $LiCoO_2$ results in a higher discharge potential of the flow battery. If one mediator cannot satisfy the conditions, two or more mediators are used for charge-discharge.

When the first active material 310 is $LiCoO_2$, therefore, the discharge potential of a flow battery can be increased by using at least one heteroaromatic compound as a charge mediator of the first electrode mediator 111 and by using, as a discharge mediator, a heteroaromatic compound that causes a reversible single- or multi-step redox reaction at 3.74 V vs. $Li/Li^+$. The heteroaromatic compound(s) used as a charge mediator may be at least one selected from the group consisting of thianthrene, phenoxathiin, dibenzo[b,e][1,4]dioxin, and tetrathiafulvalenes. The heteroaromatic compound used as a discharge mediator may be 2,2'-bithiophene. In this case, the discharge potential can be increased by approximately 0.4 to 0.5 V compared with using $LiFePO_4$, which has a discharge potential of approximately 3.5 V, as a solid positive-electrode active material.

A heteranthrene compound may be used as a charge mediator. In this case, a mediator with a redox potential lower than the equilibrium potential of a solid positive-electrode active material may be used as a discharge mediator.

In the flow battery 1000 according to the first embodiment, the first liquid 110 may further contain a first electrode side discharge mediator 112 dissolved therein. In other words, the first liquid 110 may further contain a first electrode side discharge mediator 112.

In this case, the first active material 310 may have an equilibrium potential lower than the oxidation potential $E_{ox}$ of the heteranthrene compound.

Furthermore, the first active material 310 may have an equilibrium potential higher than the equilibrium potential of the first electrode side discharge mediator.

In such a structure, the use of an active material with an equilibrium potential lower than the oxidation potential $E_{ox}$ of the heteranthrene compound as the first active material 310 allows a heteranthrene compound according to the first embodiment to function as a charge mediator. In other words, the use of an active material with an electric potential lower than the oxidation potential $E_{ox}$ as the first active material 310 allows a heteranthrene compound according to the first embodiment to function as a charge mediator. On the other hand, the use of an active material with an equilibrium potential higher than the equilibrium potential of the first electrode side discharge mediator as the first active material 310 allows the first electrode side discharge mediator to function as a discharge mediator. In other words, the use of an active material with an electric potential lower than the equilibrium potential of the first electrode side discharge mediator as the first active material 310 allows the first electrode side discharge mediator to function as a discharge mediator.

The first electrode side discharge mediator may be a heteroaromatic compound, such as 2,2'-bithiophene, and/or a cyclopentadienyl compound, such as ferrocene.

A heteranthrene compound may be used as a discharge mediator. In this case, a mediator with a redox potential higher than the equilibrium potential of a solid positive-electrode active material may be used as a charge mediator.

The first active material 310 may be a solid active material. The solid active material may be an active material powder. Storage of the first active material 310 as an unprocessed powder in a tank can simplify production and reduce production costs.

The first active material 310 may be active material pellets. The active material pellets may be formed by pelletizing an active material powder. Storage of the first active material 310 as pellets in a tank can simplify production and reduce production costs.

The first active material 310 may be an active material pelletized with a known binder. The binder may be poly (vinylidene difluoride), polypropylene, polyethylene, or polyimide.

The first active material 310 may be a substance that is insoluble in the first liquid 110. Thus, there is provided a flow battery in which the first liquid 110 and the first electrode mediator 111 circulate, but the first active material 310 does not circulate.

In the flow battery 1000 according to the first embodiment, the first liquid 110 may be at least one selected from the group consisting of propylene carbonate (PC), ethylene carbonate (EC), γ-butyrolactone, dimethyl carbonate (DMC), ethyl methyl carbonate (EMC), fluoroethylene carbonate (FEC), and diethyl carbonate (DEC). The first liquid 110 may be an ether solvent. Examples of the ether solvent include tetrahydrofuran (THF), 2-methyltetrahydrofuran (2MeTHF), dimethoxyethane (DME), 1,3-dioxane (1,3DO), and 4-methyl-1,3-dioxane (4Me1,3DO).

In the flow battery 1000 according to the first embodiment, the first liquid 110 may be an electrolytic solution containing an electrolyte in a solvent that is a material for the first liquid 110. The electrolyte (salt) may be at least one selected from the group consisting of $LiBF_4$, $LiPF_6$, and $LiN(CF_3SO_2)_2$. The solvent may have a high dielectric constant, low reactivity with Li ions, and a potential window up to approximately 4 V.

The flow battery 1000 according to the first embodiment may include the first electrode 210 as a positive electrode and a second electrode 220 as a negative electrode.

If the second electrode 220 has a relatively high electric potential, the first electrode 210 may function as a negative electrode.

Thus, the first electrode 210 may be a negative electrode, and the second electrode 220 may be a positive electrode.

In the flow battery 1000 according to the first embodiment, for example, when the first liquid 110 comes into contact with the first electrode 210, the first electrode mediator 111 is oxidized or reduced on the first electrode 210.

The first electrode 210 may have a surface acting as a reaction field for the first electrode mediator 111.

In this case, the material of the first electrode 210 may be stable in the first liquid 110. The stable material in the first liquid 110 may be a material insoluble in the first liquid 110. The material of the first electrode 210 may also be resistant to an electrode reaction, that is, an electrochemical reaction. For example, the first electrode 210 may be formed of a metal or carbon. Examples of the metal include stainless steel, iron, copper, and nickel.

The first electrode 210 may have an increased surface area. Examples of such a structure with an increased surface area include meshes, nonwoven fabrics, surface-roughened sheets, and sintered porous bodies. Thus, the first electrode 210 may have an increased specific surface area. This can promote an oxidation or reduction reaction of the first electrode mediator 111.

The second electrode 220 may include a current collector and an active material on the current collector. Thus, for example, a high-capacity active material may be used. An active material of the second electrode 220 may be a compound that reversibly occludes and releases lithium ions.

The second electrode 220 may be made of lithium metal. The second electrode 220 made of lithium metal can easily control dissolution and precipitation as a metal positive electrode and achieve high capacity.

The flow battery 1000 according to the first embodiment may further include a separator (hereinafter referred to as separating unit) 400.

The separating unit 400 separates the first electrode 210 and the first liquid 110 from the second electrode 220.

The separating unit 400 may be a microporous membrane and/or a porous body for use in known secondary batteries.

The separating unit 400 may be a porous film, such as glass paper, which is a nonwoven fabric with glass fibers woven in.

The separating unit 400 may be a membrane with ionic conductivity, such as a lithium-ion-conducting membrane. For example, the separating unit 400 may be an ion-exchange resin membrane or a solid electrolyte membrane. The ion-exchange resin membrane may be a cation-exchange membrane or an anion-exchange membrane.

The first circulation mechanism 510 circulates the first liquid 110 between the first electrode 210 and the first active material 310.

Such a structure can circulate the first electrode mediator 111 together with the first liquid 110 between the first electrode 210 and the first active material 310. This can efficiently promote an oxidation reaction and a reduction reaction between materials.

The first circulation mechanism 510 may include a pipe, a tank, a pump, and a valve, for example.

A specific example of the first circulation mechanism 510 may be a structure described later in a second embodiment.

Charge-Discharge Process

The charge-discharge process of the flow battery 1000 according to the first embodiment will be described below.

The charge-discharge process is specifically described with the following operation example.

In the operation example, the first electrode 210 is a positive electrode made of carbon black.

In the operation example, the first liquid 110 is an ether solution containing the first electrode mediator 111 dissolved therein.

In the operation example, the first electrode mediator 111 is a heteranthrene compound (hereinafter referred to as heteranthrene) according to the first embodiment.

In the operation example, the first active material 310 is lithium cobalt oxide ($LiCoO_2$).

In the operation example, the second electrode 220 is a negative electrode made of lithium metal.

Charging Process

First, a charge reaction will be described below.

A voltage is applied between the first electrode 210 and the second electrode 220 for charging.

Reaction on Negative Electrode

Upon application of a voltage, electrons are supplied to the negative electrode, that is, to the second electrode 220 from the outside of the flow battery. A reduction reaction occurs on the negative electrode, that is, on the second electrode 220. Thus, the negative electrode is charged.

For example, the following reaction occurs in the operation example.

$$Li^+ + e^- \rightarrow Li$$

Reaction on Positive Electrode

Upon application of a voltage, an oxidation reaction of the first electrode mediator 111 occurs on the positive electrode, that is, on the first electrode 210. Thus, the first electrode mediator 111 is oxidized on the surface of the first electrode 210. Thus, electrons are released from the first electrode 210 to the outside of the flow battery.

For example, the following reaction occurs in the operation example.

$$\text{heteranthrene} \rightarrow \text{heteranthrene}^+ + e^-$$

The first circulation mechanism 510 transfers the first electrode mediator 111 oxidized on the first electrode 210 to the first active material 310. In other words, the first circulation mechanism 510 supplies the first electrode mediator 111 oxidized on the first electrode 210 to the first active material 310.

The first electrode mediator 111 oxidized on the first electrode 210 is reduced by the first active material 310. In other words, the first active material 310 is oxidized by the first electrode mediator 111. Thus, the first active material 310 releases lithium ions.

For example, the following reaction occurs in the operation example.

$$LiCoO_2 + \text{heteranthrene}^+ \rightarrow CoO_2 + Li^+ + \text{heteranthrene}$$

The first circulation mechanism 510 transfers the first electrode mediator 111 reduced by the first active material 310 to the first electrode 210. In other words, the first circulation mechanism 510 supplies the first electrode mediator 111 reduced by the first active material 310 to the first electrode 210.

Thus, the first electrode mediator 111 is oxidized on the surface of the first electrode 210.

For example, the following reaction occurs in the operation example.

$$\text{heteranthrene} \rightarrow \text{heteranthrene}^+ + e^-$$

Part of the lithium ions ($Li^+$) released from the first active material 310 may move to the second electrode 220 through the separating unit 400.

Thus, the first electrode mediator 111 is unchanged in the whole reaction including circulation.

Meanwhile, the first active material 310 separated from the first electrode 210 is charged.

Thus, heteranthrene$^+$ functions as a charge mediator on the first electrode 210, that is, as a first electrode side charge mediator.

In the fully charged state, the first liquid 110 contains heteranthrene$^+$, and the first active material 310 is $CoO_2$. The charge potential depends on the oxidation potential with respect to the direction toward heteranthrene$^+$.

The charge reaction can continue until the first active material 310 or the second electrode 220 reaches the fully charged state.

Discharge Process

A discharge reaction starting from the fully charged state will be described below.

In the fully charged state, the first active material 310 and the second electrode 220 are in the charged state.

During the discharge reaction, electric power is generated between the first electrode 210 and the second electrode 220.

Reaction on Negative Electrode

An oxidation reaction occurs on the negative electrode, that is, on the second electrode 220. Thus, the negative electrode is in a discharged state.

Thus, electrons are released from the second electrode 220 to the outside of the flow battery.

For example, the following reaction occurs in the operation example.

$$Li \rightarrow Li^+ + e^-$$

Reaction on Positive Electrode

When the flow battery is discharged, electrons are supplied to the positive electrode, that is, to the first electrode 210 from the outside of the flow battery.

Thus, a reduction reaction of the first electrode mediator 111 occurs on the first electrode 210.

Thus, the first electrode mediator 111 is reduced on the surface of the first electrode 210.

For example, the following reaction occurs in the operation example.

$$\text{heteranthrene}^+ + e^- \rightarrow \text{heteranthrene}$$

The first circulation mechanism 510 transfers the first electrode mediator 111 reduced on the first electrode 210 to the first active material 310. In other words, the first circulation mechanism 510 supplies the first electrode mediator 111 reduced on the first electrode 210 to the first active material 310.

The first electrode mediator 111 reduced on the first electrode 210 is oxidized by the first active material 310. In other words, the first active material 310 is reduced by the first electrode mediator 111. Thus, the first active material 310 occludes lithium.

For example, the following reaction occurs in the operation example.

$$CoO_2 + Li^+ + \text{heteranthrene} \rightarrow LiCoO_2 + \text{heteranthrene}^+$$

The first circulation mechanism 510 transfers (supplies) the first electrode mediator 111 oxidized by the first active material 310 to the first electrode 210. In other words, the first circulation mechanism 510 supplies the first electrode mediator 111 oxidized by the first active material 310 to the first electrode 210.

Thus, the first electrode mediator 111 is reduced on the surface of the first electrode 210.

For example, the following reaction occurs in the operation example.

$$\text{heteranthrene}^+ + e^- \rightarrow \text{heteranthrene}$$

Lithium ions (Li$^+$) may be partly supplied from the second electrode 220 through the separating unit 400.

Thus, the first electrode mediator 111 is unchanged in the whole reaction including circulation.

Meanwhile, the first active material 310 separated from the first electrode 210 is in the discharged state.

Thus, heteranthrene functions as a discharge mediator on the first electrode 210, that is, as a first electrode side discharge mediator.

In the fully discharged state, the first liquid 110 contains heteranthrene, and the first active material 310 is LiCoO$_2$. The discharge potential depends on the reduction potential with respect to the direction toward heteranthrene.

The discharge reaction can continue until the first active material 310 or the second electrode 220 reaches the fully discharged state.

Second Embodiment

A second embodiment will be described below. The contents described in the first embodiment are appropriately omitted to avoid overlap.

Figure 2:
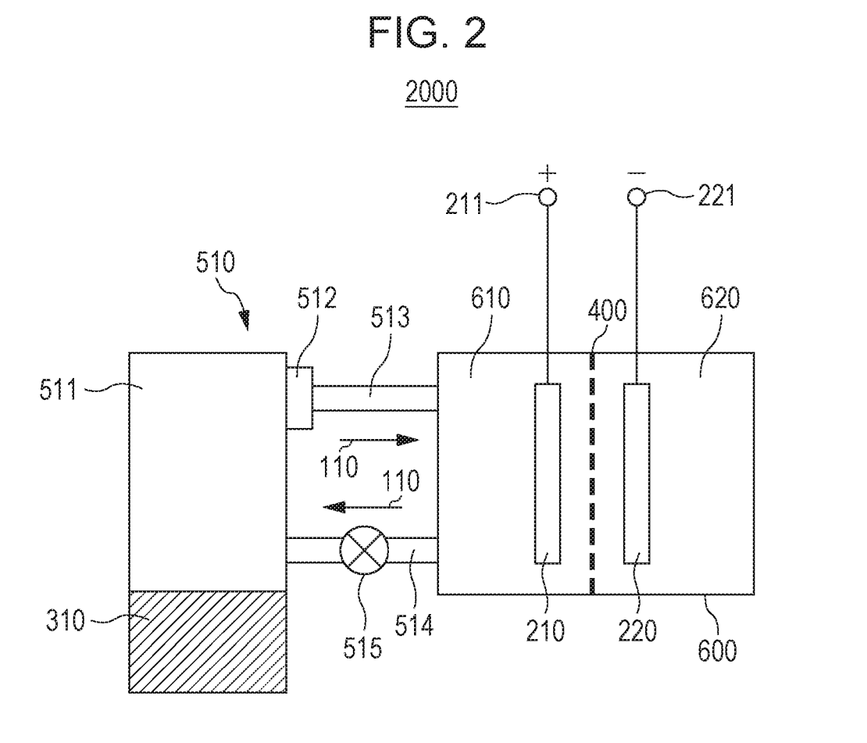
FIG. 2 is a schematic view of a flow battery according to a second embodiment.

FIG. 2 is a schematic view of a flow battery 2000 according to the second embodiment.

In addition to the components of the flow battery 1000 according to the first embodiment, the flow battery 2000 according to the second embodiment further includes the following components.

In the flow battery 2000 according to the second embodiment, the first circulation mechanism 510 includes a first container 511.

The first active material 310 and the first liquid 110 are contained in the first container 511.

The first circulation mechanism 510 circulates the first liquid 110 between the first electrode 210 and the first container 511.

Contact between the first active material 310 and the first liquid 110 in the first container 511 causes at least one of an oxidation reaction and a reduction reaction of the first electrode mediator 111 with the first active material 310.

In such a structure, the first liquid 110 can come into contact with the first active material 310 in the first container 511. This can increase the contact area between the first liquid 110 and the first active material 310, for example. This can also increase the contact time between the first liquid 110 and the first active material 310. This can efficiently promote an oxidation reaction and a reduction reaction of the first electrode mediator 111 with the first active material 310.

In the second embodiment, the first container 511 may be a tank.

The first container 511 may contain the first liquid 110, which contains the first electrode mediator 111 dissolved therein, in voids of the first active material 310.

The first container 511 may contain the first liquid 110, which contains the first electrode mediator 111 dissolved therein, in voids of the first active material 310.

As illustrated in FIG. 2, the flow battery 2000 according to the second embodiment may further include an electrochemical reaction unit 600, a positive-electrode terminal 211, and a negative-electrode terminal 221.

The electrochemical reaction unit 600 is divided into a positive-electrode chamber 610 and a negative-electrode chamber 620 by the separating unit 400.

An electrode acting as a positive electrode is disposed in the positive-electrode chamber 610. In FIG. 2, the first electrode 210 is disposed in the positive-electrode chamber 610.

The positive-electrode terminal 211 is coupled to the electrode acting as a positive electrode.

An electrode acting as a negative electrode is disposed in the negative-electrode chamber 620. In FIG. 2, the second electrode 220 is disposed in the negative-electrode chamber 620.

The negative-electrode terminal 221 is coupled to the electrode acting as a negative electrode.

The positive-electrode terminal 211 and the negative-electrode terminal 221 are coupled to a charge-discharge apparatus, for example. The charge-discharge apparatus applies a voltage between the positive-electrode terminal 211 and the negative-electrode terminal 221 or collects electric power generated between the positive-electrode terminal 211 and the negative-electrode terminal 221.

As illustrated in FIG. 2, in the flow battery 2000 according to the second embodiment, the first circulation mechanism 510 may include a pipe 514, a pipe 513, and a pump 515.

One end of the pipe 514 is coupled to the positive-electrode chamber 610 or the negative-electrode chamber 620 in which the first electrode 210 is to be disposed. In FIG. 2, one end of the pipe 514 is coupled to the positive-electrode chamber 610.

The other end of the pipe 514 is coupled to an inlet of the first container 511 for the first liquid 110.

One end of the pipe 513 is coupled to an outlet of the first container 511 for the first liquid 110.

The other end of the pipe 513 is coupled to the positive-electrode chamber 610 or the negative-electrode chamber 620 in which the first electrode 210 is to be disposed. In FIG. 2, the other end of the pipe 513 is coupled to the positive-electrode chamber 610.

The pump 515 is disposed on the pipe 514, for example. The pump 515 may be disposed on the pipe 513.

In the flow battery 2000 according to the second embodiment, the first circulation mechanism 510 may include a first transfer prevention unit 512.

The first transfer prevention unit 512 prevents the transfer of the first active material 310.

The first transfer prevention unit 512 is disposed on the path through which the first liquid 110 flows from the first container 511 to the first electrode 210. In FIG. 2, the first transfer prevention unit 512 is disposed on the pipe 513.

Such a structure can prevent the first active material 310 from flowing out of the first container 511 (for example, to the first electrode 210). Thus, the first active material 310 remains in the first container 511. Thus, the first active material 310 does not circulate in the flow battery. This can prevent clogging of a component in the first circulation mechanism 510 with the first active material 310. The component in the first circulation mechanism 510 is a pipe, for example. This can also prevent resistive loss due to the first active material 310 flowing to the first electrode 210.

The first transfer prevention unit 512 may be disposed on the joint between the first container 511 and the pipe 513.

For example, the first transfer prevention unit 512 is a filter that filters out the first active material 310. The filter may have openings smaller than the smallest particles of the first active material 310. The filter may be formed of a material that does not react with the first active material 310 and the first liquid 110. The filter may be a glass fiber filter paper, polypropylene nonwoven fabric, polyethylene nonwoven fabric, or a metal mesh that does not react with metallic lithium.

Such a structure can prevent the first active material 310 from flowing out of the first container 511 even when the flow of the first liquid 110 causes the flow of the first active material 310 in the first container 511.

In FIG. 2, the first liquid 110 in the first container 511 is supplied to the positive-electrode chamber 610 through the first transfer prevention unit 512 and through the pipe 513.

Thus, the first electrode mediator 111 dissolved in the first liquid 110 is oxidized or reduced on the first electrode 210.

Subsequently, the first liquid 110 containing the oxidized or reduced first electrode mediator 111 dissolved therein is supplied to the first container 511 through the pipe 514 and through the pump 515.

Thus, the first electrode mediator 111 dissolved in the first liquid 110 causes at least one of an oxidation reaction and a reduction reaction with the first active material 310.

The circulation of the first liquid 110 may be controlled with the pump 515. More specifically, the supply of the first liquid 110 may be started or stopped with the pump 515, or the amount of the first liquid 110 may be controlled with the pump 515.

The circulation of the first liquid 110 may be controlled by another means other than the pump 515. Another means is a valve, for example.

In FIG. 2, by way of example, the first electrode 210 is a positive electrode, and the second electrode 220 is a negative electrode.

If the second electrode 220 has a relatively high electric potential, the first electrode 210 may function as a negative electrode.

Thus, the first electrode 210 may be a negative electrode, and the second electrode 220 may be a positive electrode.

Separated by the separating unit 400, the positive-electrode chamber 610 and the negative-electrode chamber 620 may contain different electrolytic solutions and/or solvents.

The positive-electrode chamber 610 and the negative-electrode chamber 620 may contain the same electrolytic solution and/or solvent.

Third Embodiment

A third embodiment will be described below. The contents described in the first or second embodiment are appropriately omitted to avoid overlap.

In the third embodiment, an electrolytic solution circulates around the first electrode and the second electrode.

Figure 3:
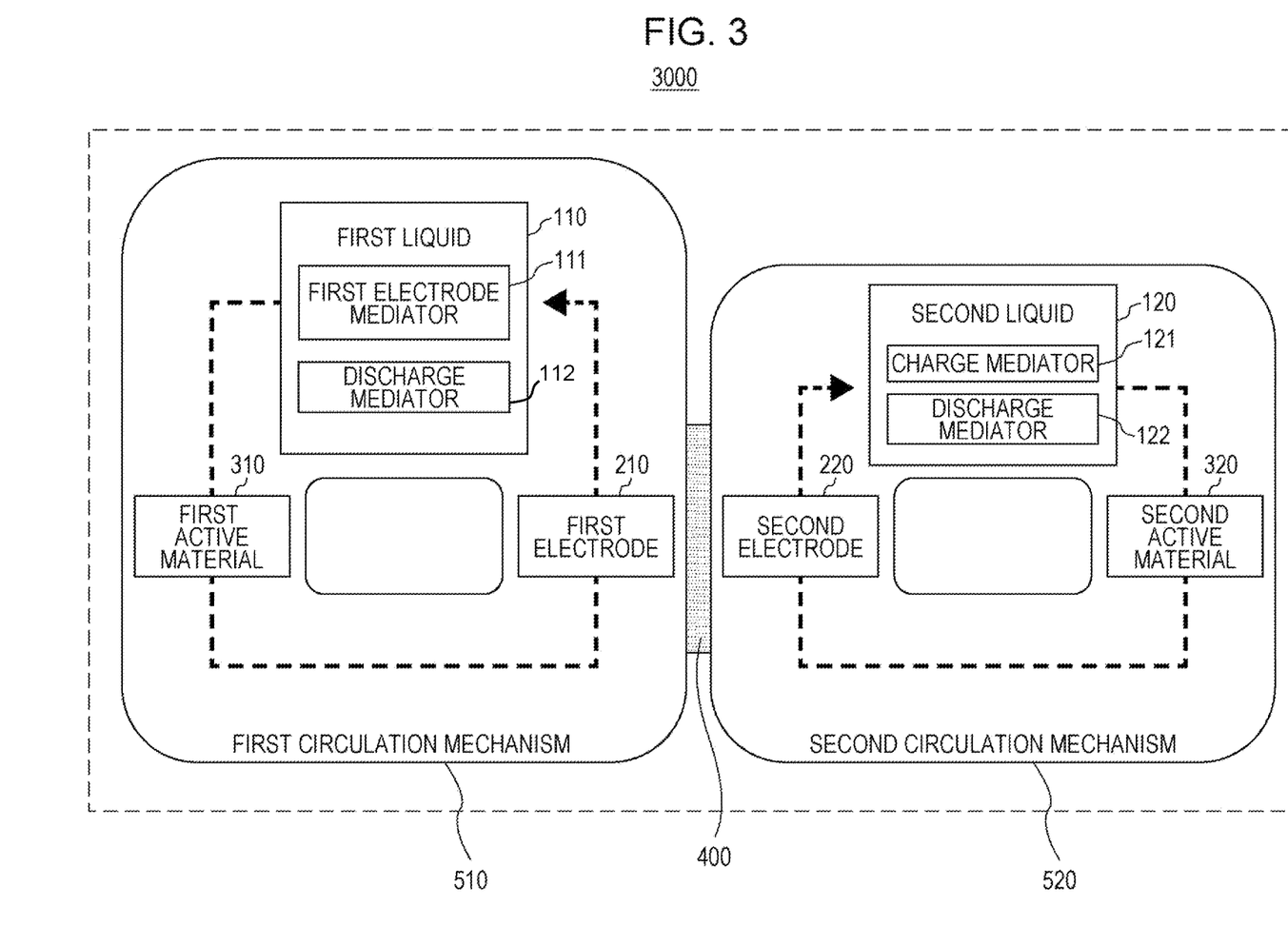
FIG. 3 is a schematic block diagram of a flow battery according to a third embodiment.

FIG. 3 is a schematic block diagram of a flow battery 3000 according to the third embodiment.

In addition to the components of the flow battery 1000 according to the first embodiment, the flow battery 3000 according to the third embodiment further includes the following components.

The flow battery 3000 according to the third embodiment further includes a second liquid 120, the second electrode 220, a second active material 320, and the separating unit 400.

The second liquid 120 contains a charge mediator 121 dissolved therein as a second electrode side charge mediator and a discharge mediator 122 dissolved therein as a second electrode side discharge mediator.

The second electrode 220 is immersed in the second liquid 120.

The second active material 320 is immersed in the second liquid 120.

The separating unit 400 separates the first electrode 210 and the first liquid 110 from the second electrode 220 and the second liquid 120.

The charge mediator 121 has a lower equilibrium potential than the second active material 320.

The discharge mediator 122 has a higher equilibrium potential than the second active material 320.

Such a structure can improve the battery voltage, energy density, and cycle life of a flow battery.

In such a structure, when the second active material 320 is an active material with a relatively low equilibrium potential (vs. Li/Li$^+$), the discharge mediator 122 may be a substance with a relatively low equilibrium potential (vs. Li/Li$^+$). Such an active material with a relatively low equilibrium potential used as the second active material 320 is graphite, for example. Such a substance with a relatively low equilibrium potential used as the discharge mediator 122 is a fused aromatic compound, for example. This can decrease the electric potential of the negative electrode of the flow battery. Thus, the flow battery can have a higher battery voltage (discharge voltage).

Furthermore, such a structure can utilize an active material for a flow battery without circulating the active material. Thus, a high-capacity active material powder can be used as the second active material 320 in a charge-discharge reaction, for example. This can increase the energy density and capacity.

Such a structure can circulate only the second liquid 120 containing the charge mediator 121 and the discharge mediator 122 dissolved therein without circulating the active material powders. This can reduce the occurrence of clogging of a pipe with the active material powder. Thus, the flow battery can have a long cycle life.

In the flow battery 3000 according to the third embodiment, the second liquid 120 may contain lithium dissolved therein.

The second active material 320 may occlude and release lithium.

When the flow battery 3000 is charged, electrons are supplied from the outside of the flow battery 3000 to the second electrode 220. When the flow battery 3000 is charged, the charge mediator 121 is reduced on the second electrode 220. When the flow battery 3000 is charged, the charge mediator 121 reduced on the second electrode 220 may be oxidized by the second active material 320, and the second active material 320 may occlude lithium.

When the flow battery 3000 is discharged, electrons are released from the second electrode 220 to the outside of the flow battery 3000. When the flow battery 3000 is discharged, the second active material 320 containing lithium reduces the discharge mediator 122 and releases lithium. When the flow battery 3000 is discharged, the discharge mediator 122 reduced by the second active material 320 may be oxidized on the second electrode 220.

In such a structure, the second active material 320 may reversibly occlude and release lithium and/or lithium ions. This facilitates the designing of the second active material 320. This can also further increase the capacity.

When the flow battery 3000 according to the third embodiment is charged, the discharge mediator 122 may be reduced on the second electrode 220.

During discharging, the charge mediator 121 may be oxidized on the second electrode 220.

Such a structure can further increase the energy density and capacity. More specifically, reduction of the discharge mediator 122 on the second electrode 220 during charging can increase the amount of the discharge mediator 122 oxidized on the second electrode 220 during discharging. Furthermore, oxidization of the charge mediator 121 on the second electrode 220 during discharging can increase the amount of the charge mediator 121 reduced on the second electrode 220 during charging. This can increase charge-discharge capacity.

In the flow battery 3000 according to the third embodiment, the charge mediator 121 and the discharge mediator 122 may be fused aromatic compounds.

The second liquid 120 containing a fused aromatic compound dissolved therein causes a solvated electron of lithium to be released and thereby dissolves the lithium as a cation.

Such a structure can decrease the electric potential of the charge mediator 121 and the discharge mediator 122. A solution containing a fused aromatic compound can dissolve lithium, for example. Such a solution containing a fused aromatic compound is an ether solution, for example. Lithium tends to release an electron and become a cation. Thus, lithium donates an electron to a fused aromatic compound in a solution and dissolves in the solution as a cation. The fused aromatic compound accepts the electron and solvates with the electron. The fused aromatic compound solvated with the electron behaves as an anion. Thus, the solution containing the fused aromatic compound is ion conductive by itself. The solution containing the fused aromatic compound contains the equivalent amounts of Li cations and electrons. Thus, the solution containing the fused aromatic compound can be highly reductive or have a low electric potential.

For example, an electrode that does not react with lithium immersed in the second liquid 120 containing a fused aromatic compound dissolved therein has a much lower electric potential than lithium metal. The electric potential depends on the degree of solvation between the fused aromatic compound and an electron, that is, on the type of fused aromatic compound. Examples of the fused aromatic compound with a low electric potential include phenanthrene, biphenyl, o-terphenyl, triphenylene, anthracene, phenanthroline, 2,2'-bipyridyl, benzophenone, trans-stilbene, 4,4'-bipyridyl, 3,3'-bipyridyl, 2,4'-bipyridyl, 2,3'-bipyridyl, and cis-stilbene. Acetophenone, propiophenone, butyrophenone, valerophenone, or ethylenediamine may be used instead of the fused aromatic compound.

In the flow battery 3000 according to the third embodiment, the charge mediator 121 may be at least one selected from the group consisting of phenanthrene, biphenyl, o-terphenyl, triphenylene, and anthracene.

Such a structure can decrease the electric potential of the charge mediator 121. More specifically, the charge mediator 121 can have a lower electric potential (vs. Li/Li$^+$) than the second active material 320. The second active material 320 is graphite, for example.

In the flow battery 3000 according to the third embodiment, the discharge mediator 122 may be at least one selected from the group consisting of phenanthroline, 2,2'-bipyridyl, benzophenone, trans-stilbene, 4,4'-bipyridyl, 3,3'-bipyridyl, 2,4'-bipyridyl, 2,3'-bipyridyl, cis-stilbene, acetophenone, propiophenone, butyrophenone, valerophenone, and ethylenediamine.

Such a structure can increase the electric potential of the discharge mediator 122. More specifically, the discharge mediator 122 can have a higher electric potential (vs. Li/Li$^+$) than the second active material 320. The second active material 320 is graphite, for example.

In the flow battery 3000 according to the third embodiment, the discharge mediator 122 may be at least one selected from the group consisting of 2,2'-bipyridyl, trans-stilbene, 2,4'-bipyridyl, 2,3'-bipyridyl, cis-stilbene, propiophenone, butyrophenone, valerophenone, and ethylenediamine.

Such a structure can decrease the equilibrium potential (vs. Li/Li$^+$) of the discharge mediator 122. This can decrease the electric potential of the negative electrode of the flow battery. Thus, the flow battery can have a higher battery voltage (discharge voltage).

In the flow battery 3000 according to the third embodiment, the second liquid 120 may be an ether solution.

In such a structure, the second liquid 120 can be an electrolytic solution containing the charge mediator 121 and the discharge mediator 122. More specifically, the solvent of the charge mediator 121 and the discharge mediator 122 is an electronically non-conductive ether solution, and the ether solution itself can have the properties of an electrolytic solution.

Examples of ether include tetrahydrofuran (THF), 2-methyltetrahydrofuran (2MeTHF), dimethoxyethane (DME), 1,3-dioxane (1,3DO), and 4-methyl-1,3-dioxane (4Me1,3DO).

In the flow battery 3000 according to the third embodiment, the second active material 320 may be graphite.

Such a structure can decrease the equilibrium potential (vs. Li/Li$^+$) of the second active material 320. Thus, the discharge mediator 122 can be a substance with a relatively low equilibrium potential (vs. Li/Li$^+$). Such a substance with a relatively low equilibrium potential for use as the discharge mediator 122 is a fused aromatic compound, for example. This can decrease the electric potential of the negative electrode of the flow battery. Thus, the flow battery can have a high battery voltage (discharge voltage).

In the third embodiment, graphite of the second active material 320 on which lithium is occluded or a graphite interlayer compound produced during charging may have a composition of at least one of $C_{24}Li$, $C_{18}Li$, $C_{12}Li$, and $C_6Li$.

When the second active material 320 is graphite ($C_6Li$), charging involves complete reduction by lithium. Thus, graphite occludes lithium to yield $C_6Li$. $C_6Li$ has an electric potential of approximately 0.2 V vs. Li/Li$^+$. Thus, a mediator-type negative electrode can be formed by using a fused aromatic compound with a lower electric potential than $C_6Li$ as a charge mediator and by using a fused aromatic compound with a higher electric potential than $C_6Li$ as a discharge mediator.

Table 2 lists the electric potentials of fused aromatic compounds usable as a charge mediator 121.

TABLE 2

| Compound | Molar concentration (M) | Electric potential (V vs. Li/Li+) |
|---|---|---|
| <br>Phenanthrene | 1 | 0.03 |

TABLE 2-continued

| Compound | Molar concentration (M) | Electric potential (V vs. Li/Li+) |
|---|---|---|
| Biphenyl | 1 | 0 |
| o-Terphenyl | 1 | 0.15 |
| Triphenylene | 0.1 | 0.01 |
| Anthracene | 0.1 | 0.05 |

Table 3 lists the electric potentials of fused aromatic compounds usable as a discharge mediator 122.

TABLE 3

| Compound | Molar concentration (M) | Electric potential (V vs. Li/Li$^+$) |
|---|---|---|
| Phenanthroline | 0.1 | 1.78 |
| 2,2'-Bipyridyl | 1 | 0.4 |
| Benzophenone | 1 | 0.78 |
| trans-Stilbene | 0.5 | 0.3 |
| 4,4'-Bipyridyl | 0.1 | 1.22 |
| 3,3'-Bipyridyl | 0.1 | 2.5 |
| 2,4'-Bipyridyl | 0.1 | 0.54 |
| 2,3'-Bipyridyl | 0.1 | 0.58 |
| cis-Stilbene | 0.1 | 0.43 |
| Acetophenone | 0.1 | 1.29 |
| Propiophenone | 0.1 | 0.42 |

TABLE 3-continued

| Compound | Molar concentration (M) | Electric potential (V vs. Li/Li+) |
|---|---|---|
| Butyrophenone | 0.1 | 0.3 |
| Valerophenone | 0.1 | 0.31 |
| Ethylenediamine | 0.1 | 0.36 |

A 2×2 cm² copper foil is covered with a polypropylene microporous separator, which is covered with a large amount of lithium metal foil. A tab is attached to the copper foil and lithium metal. Subsequently, a laminate exterior is attached. After pouring 2MeTHF in which a fused aromatic compound is dissolved at a molar concentration (M) listed in Tables 2 and 3, the laminate exterior is hermetically sealed by heat. Thus, an electrometric cell for each fused aromatic compound is prepared. Tables 2 and 3 list the electric potentials (V vs. Li/Li+) based on lithium metal measured with the electrometric cells. Although 2MeTHF can be used in this measurement, another ether may also be used.

The charge mediator 121 cannot dissolve Li of $C_6Li$. By contrast, the discharge mediator 122 can dissolve Li of $C_6Li$. This difference results from the difference between the electric potential of $C_6Li$ and the electric potentials of these lithium metal solutions. Those with a higher electric potential than $C_6Li$ (approximately 0.2 V vs. Li/Li+) can dissolve Li of $C_6Li$. By contrast, those with a lower electric potential than $C_6Li$ cannot dissolve Li of $C_6Li$.

Thus, those with a lower electric potential than $C_6Li$ can be used as the charge mediator 121. Those with a higher electric potential than $C_6Li$ can be used as the discharge mediator 122.

A smaller potential difference between the fused aromatic compound and the second active material 320 results in higher charge-discharge energy efficiency. When the second active material 320 is graphite ($C_6Li$), therefore, the charge mediator 121 may be phenanthrene, triphenylene, or biphenyl. The discharge mediator 122 may be trans-stilbene, butyrophenone, valerophenone, or ethylenediamine. This can further increase charge-discharge energy efficiency.

Unlike Li ions, the ether may not be intercalated into graphite. No co-intercalation of Li and the ether in graphite can increase the capacity density.

The second active material 320 may be a solid active material. The solid active material may be an active material powder. Storage of the second active material 320 as an unprocessed powder in a tank can simplify production and reduce production costs.

The second active material 320 may be active material pellets. The active material pellets may be formed by pelletizing an active material powder. Storage of the second active material 320 as pellets in a tank can simplify production and reduce production costs.

The second active material 320 may be an active material pelletized with a known binder. The binder may be poly (vinylidene difluoride), polypropylene, polyethylene, or polyimide.

The second active material 320 may be a substance that is insoluble in the second liquid 120. Thus, there is provided a flow battery in which the charge mediator 121 and the discharge mediator 122 as well as the second liquid 120 circulate, but the second active material 320 does not circulate.

In the flow battery 3000 according to the third embodiment, the second electrode 220 may be a negative electrode, and the first electrode 210 may be a positive electrode.

If the first electrode 210 has a relatively low electric potential, the second electrode 220 may function as a positive electrode.

Thus, the second electrode 220 may be a positive electrode, and the first electrode 210 may be a negative electrode.

In the flow battery 3000 according to the third embodiment, for example, when the second liquid 120 comes into contact with the second electrode 220, the charge mediator 121 and the discharge mediator 122 are oxidized or reduced on the second electrode 220. For example, when the second liquid 120 comes into contact with the second active material 320, the second active material 320 causes a reduction reaction of the discharge mediator 122 or an oxidation reaction of the charge mediator 121.

The second electrode 220 may have a surface that acts as a reaction field for the charge mediator 121 and the discharge mediator 122.

In this case, the material of the second electrode 220 may be stable in the second liquid 120. The stable material in the second liquid 120 may be a material insoluble in the second liquid 120. The material of the second electrode 220 may also be resistant to an electrode reaction, that is, an electrochemical reaction. For example, the second electrode 220 may be formed of a metal or carbon. Examples of the metal include stainless steel, iron, copper, and nickel.

The second electrode 220 may have an increased surface area. Examples of such a structure with an increased surface area include meshes, nonwoven fabrics, surface-roughened sheets, and sintered porous bodies. Thus, the second electrode 220 may have a large specific surface area. This can promote an oxidation or reduction reaction of the charge mediator 121 and the discharge mediator 122.

The flow battery 3000 according to the third embodiment may further include a second circulator (hereinafter referred to as second circulation mechanism) 520.

The second circulation mechanism 520 circulates the second liquid 120 between the second electrode 220 and the second active material 320.

Such a structure can circulate the charge mediator 121 and the discharge mediator 122 together with the second liquid 120 between the second electrode 220 and the second active material 320. This can efficiently promote an oxidation reaction and a reduction reaction between materials.

The second circulation mechanism 520 may include a pipe, a tank, a pump, and a valve, for example.

A specific example of the second circulation mechanism 520 may be a structure described later in a fourth embodiment.

Charge-Discharge Process

The charge-discharge process of the flow battery 3000 according to the third embodiment will be described below.

The charge-discharge process is specifically described with the following operation example.

In the operation example, the first electrode 210 is a positive electrode made of carbon black.

In the operation example, the first liquid 110 is an ether solution containing the first electrode mediator 111 dissolved therein.

In the operation example, the first electrode mediator 111 is a heteranthrene compound (hereinafter referred to as heteranthrene) according to the first embodiment.

In the operation example, the first active material 310 is lithium cobalt oxide ($LiCoO_2$).

In the operation example, the second electrode 220 is a negative electrode made of stainless steel.

In the operation example, the second liquid 120 is an ether solution containing the charge mediator 121 and the discharge mediator 122 dissolved therein.

In the operation example, the charge mediator 121 on the side of the second electrode 220 is a fused aromatic compound (hereinafter referred to as ChMd).

In the operation example, the discharge mediator 122 on the side of the second electrode 220 is a fused aromatic compound (hereinafter referred to as DchMd).

In the operation example, the second active material 320 is graphite ($C_6Li$).

In the operation example, the separating unit 400 is a lithium ion conductive solid electrolyte membrane.

Charging Process

First, a charge reaction will be described below.

A voltage is applied between the first electrode 210 and the second electrode 220 for charging.

Reaction on Negative Electrode

Upon application of a voltage, electrons are supplied to the negative electrode, that is, to the second electrode 220 from the outside of the flow battery. This causes a reduction reaction of the charge mediator 121 and the discharge mediator 122 on the second electrode 220.

For example, the following reaction occurs in the operation example.

$$ChMd + Li^+ + e^- \rightarrow ChMd.Li$$

$$DchMd + Li^+ + e^- \rightarrow DchMd.Li$$

The second circulation mechanism 520 transfers the charge mediator 121 reduced on the second electrode 220 to the second active material 320. In other words, the second circulation mechanism 520 supplies the charge mediator 121 reduced on the second electrode 220 to the second active material 320.

The charge mediator 121 reduced on the second electrode 220 is oxidized by the second active material 320. In other words, the second active material 320 is reduced by the charge mediator 121. Thus, the second active material 320 occludes lithium and becomes $C_6Li$.

For example, the following reaction occurs in the operation example.

$$6C + ChMd.Li \rightarrow C_6Li + ChMd$$

The second circulation mechanism 520 transfers the charge mediator 121 oxidized by the second active material 320 to the second electrode 220. In other words, the second circulation mechanism 520 supplies the charge mediator 121 oxidized by the second active material 320 to the second electrode 220.

Thus, the charge mediator 121 is unchanged in the whole reaction including circulation.

Meanwhile, the second active material 320 separated from the second electrode 220 is charged.

Reaction on Positive Electrode

Upon application of a voltage, an oxidation reaction of the first electrode mediator 111 occurs on the positive electrode, that is, on the first electrode 210. Thus, the first electrode mediator 111 is oxidized on the surface of the first electrode 210. Thus, electrons are released from the first electrode 210 to the outside of the flow battery.

For example, the following reaction occurs in the operation example.

$$heteranthrene \rightarrow heteranthrene^+ + e^-$$

The first circulation mechanism 510 transfers the first electrode mediator 111 oxidized on the first electrode 210 to the first active material 310. In other words, the first circulation mechanism 510 supplies the first electrode mediator 111 oxidized on the first electrode 210 to the first active material 310.

The first electrode mediator 111 oxidized on the first electrode 210 is reduced by the first active material 310. In other words, the first active material 310 is oxidized by the first electrode mediator 111. Thus, the first active material 310 releases lithium.

For example, the following reaction occurs in the operation example.

$$LiCoO_2 + heteranthrene^+ \rightarrow CoO_2 + Li^+ + heteranthrene^+$$

The first circulation mechanism 510 transfers the first electrode mediator 111 reduced by the first active material 310 to the first electrode 210. In other words, the first circulation mechanism 510 supplies the first electrode mediator 111 reduced by the first active material 310 to the first electrode 210.

Thus, the first electrode mediator 111 is oxidized on the surface of the first electrode 210.

For example, the following reaction occurs in the operation example.

$$heteranthrene \rightarrow heteranthrene^+ + e^-$$

Part of lithium ions ($Li^+$) thus released may move to the second electrode 220 through the separating unit 400.

Thus, the first electrode mediator 111 is unchanged in the whole reaction including circulation.

Meanwhile, the first active material 310 separated from the first electrode 210 is charged.

Thus, heteranthrene$^+$ functions as a charge mediator on the first electrode 210, that is, as a first electrode side charge mediator.

In the fully charged state, the first liquid 110 contains heteranthrene$^+$, and the first active material 310 is $LiCoO_2$. The charge potential depends on the oxidation potential with respect to the direction toward heteranthrene$^+$.

The charge reaction can continue until the first active material 310 or the second active material 320 reaches the fully charged state.

Discharge Process

A discharge reaction starting from the fully charged state will be described below.

In the fully charged state, the first active material 310 and the second active material 320 are in the charged state.

During the discharge reaction, electric power is generated between the first electrode 210 and the second electrode 220.

Reaction on Negative Electrode

Battery discharge causes an oxidation reaction of the charge mediator 121 and the discharge mediator 122 on the negative electrode, that is, on the second electrode 220. Thus, electrons are released from the second electrode 220 to the outside of the flow battery.

For example, the following reaction occurs in the operation example.

DchMd.Li→DchMd+Li$^+$+e$^-$

ChMd.Li→ChMd+Li$^+$+e$^-$

The second circulation mechanism 520 transfers the discharge mediator 122 oxidized on the second electrode 220 to the second active material 320. In other words, the second circulation mechanism 520 supplies the discharge mediator 122 oxidized on the second electrode 220 to the second active material 320.

The discharge mediator 122 oxidized on the second electrode 220 is reduced by the second active material 320. In other words, the second active material 320 is oxidized by the discharge mediator 122. Thus, the second active material 320 releases lithium.

For example, the following reaction occurs in the operation example.

C$_6$Li+DchMd→6C+DchMd.Li

The second circulation mechanism 520 transfers the discharge mediator 122 reduced by the second active material 320 to the second electrode 220. In other words, the second circulation mechanism 520 supplies the discharge mediator 122 reduced by the second active material 320 to the second electrode 220.

Thus, the discharge mediator 122 is unchanged in the whole reaction including circulation.

Meanwhile, the second active material 320 separated from the second electrode 220 is in the discharged state.

Reaction on Positive Electrode

When the flow battery is discharged, electrons are supplied to the positive electrode, that is, to the first electrode 210 from the outside of the flow battery. Thus, a reduction reaction of the first electrode mediator 111 occurs on the first electrode 210. Thus, the first electrode mediator 111 is reduced on the surface of the first electrode 210.

For example, the following reaction occurs in the operation example.

heteranthrene$^+$+e$^-$→heteranthrene

The first circulation mechanism 510 transfers the first electrode mediator 111 reduced on the first electrode 210 to the first active material 310. In other words, the first circulation mechanism 510 supplies the first electrode mediator 111 reduced on the first electrode 210 to the first active material 310.

The first electrode mediator 111 reduced on the first electrode 210 is oxidized by the first active material 310. In other words, the first active material 310 is reduced by the first electrode mediator 111. Thus, the first active material 310 occludes lithium.

For example, the following reaction occurs in the operation example.

CoO$_2$+Li$^+$+heteranthrene→LiCoO$_2$+heteranthrene$^+$

The first circulation mechanism 510 transfers the first electrode mediator 111 oxidized by the first active material 310 to the first electrode 210. In other words, the first circulation mechanism 510 supplies the first electrode mediator 111 oxidized by the first active material 310 to the first electrode 210.

Thus, the first electrode mediator 111 is reduced on the surface of the first electrode 210.

For example, the following reaction occurs in the operation example.

heteranthrene$^+$+e$^-$→heteranthrene

Lithium ions (Li$^+$) may be partly supplied from the second electrode 220 through the separating unit 400.

Thus, the first electrode mediator 111 is unchanged in the whole reaction including circulation.

Meanwhile, the first active material 310 separated from the first electrode 210 is in the discharged state.

Thus, heteranthrene functions as a discharge mediator on the first electrode 210, that is, as a first electrode side discharge mediator.

In the fully discharged state, the first liquid 110 contains heteranthrene, and the first active material 310 is LiCoO$_2$. The discharge potential depends on the reduction potential with respect to the direction toward heteranthrene.

The discharge reaction can continue until the first active material 310 or the second active material 320 reaches the fully discharged state.

Estimation of Energy Density

The estimated energy density of the flow battery 3000 according to the third embodiment will be described below.

Table 4 lists the estimated energy densities of the flow battery 3000 according to the third embodiment.

TABLE 4

| Positive-electrode charge mediator | Thianthrene | Phenoxathiin | Dibenzo[b,e][1,4]dioxin | TTF (reference) |
|---|---|---|---|---|
| Positive-electrode charge mediator potential (V vs. Li/Li$^+$) | 4.60 | 4.65 | 4.34 | 3.64 |
| Positive-electrode discharge mediator potential (V vs. Li/Li$^+$) | 4.01 | 3.80 | 3.74 | 3.29 |
| Negative-electrode charge mediator potential (V vs. Li/Li$^+$) | 0.03 | 0.03 | 0.03 | 0.03 |
| Negative-electrode discharge mediator potential (V vs. Li/Li$^+$) | 0.30 | 0.30 | 0.30 | 0.3 |
| Flow battery charge voltage (V) | 4.57 | 4.62 | 4.31 | 3.61 |
| Flow battery discharge voltage (V) | 3.71 | 3.50 | 3.44 | 2.99 |
| Flow battery theoretical capacity density (Ah/L) | 521.53 | 521.53 | 521.53 | 353.52 |
| Flow battery theoretical energy density (Wh/L) | 1934.87 | 1825.35 | 1794.06 | 1055.95 |
| Volume filling factor of electricity generating element | 0.60 | 0.60 | 0.60 | 0.6 |
| Flow battery energy density (Wh/L) | 1160.92 | 1095.21 | 1076.43 | 633.57 |

Negative electrode: graphite, positive electrode: LiCoO$_2$
Positive-electrode charge mediator: heteranthrene molecule (E1 = 3.8-4.3 V, E2 = 4.5-4.6 V)
Positive-electrode discharge mediator: heteranthrene molecule (two-step redox reaction) or 2,2'-bithiophene (3.74 V)
Calculated on the assumption that the negative-electrode charge mediator is phenanthrene (0.03 V), and the negative-electrode discharge mediator is stilbene (0.3 V)

Table 4 lists the estimated energy densities under the conditions of the operation example of the flow battery 3000 according to the third embodiment. Each of the heteranthrene compounds listed in Table 1 is used as a charge mediator of the first electrode mediator 111. For a positive-electrode charge mediator that causes a one-step redox reaction, 2,2'-bithiophene is used as a positive-electrode discharge mediator. The charge mediator 121 is phenanthrene, and the discharge mediator 122 is trans-stilbene. The volume filling factor of electricity generating element in Table 4 represents the percentage. For example, a volume filling factor of 0.60 means 60%.

In Table 4, in the calculation example in which tetrathiafulvalene is used as the first electrode mediator 111, that is, as a positive-electrode charge mediator, the solid positive-electrode active material is $LiFePO_4$, and 2,2'-bithiophene is not used. This is because tetrathiafulvalene (TTF) also functions as a positive-electrode discharge mediator.

Table 4 shows that the flow battery has an energy density of approximately 1076 Wh/L when the charge mediator is dibenzo[b,e][1,4]dioxin and the discharge mediator is a heteroaromatic compound, such as 2,2'-bithiophene, as the first electrode mediator 111. The flow battery has an energy density of approximately 1100 Wh/L when the charge-discharge mediator is thianthrene or phenoxathiin as the first electrode mediator 111.

By contrast, known flow batteries utilizing vanadium have a theoretical energy density of approximately 38 Wh/L. Thus, the flow batteries according to the present disclosure have significantly higher theoretical energy densities than known flow batteries.

Table 4 also shows that when tetrathiafulvalene is used as the first electrode mediator 111, $LiFePO_4$ is used as the solid positive-electrode active material, and the flow battery has an energy density of approximately 633 Wh/L. These results show that a flow battery containing a heteranthrene compound has a higher theoretical energy density than those containing tetrathiafulvalene or a derivative thereof.

Fourth Embodiment

A fourth embodiment will be described below. The contents described in the first to third embodiments are appropriately omitted to avoid overlap.

Figure 4:
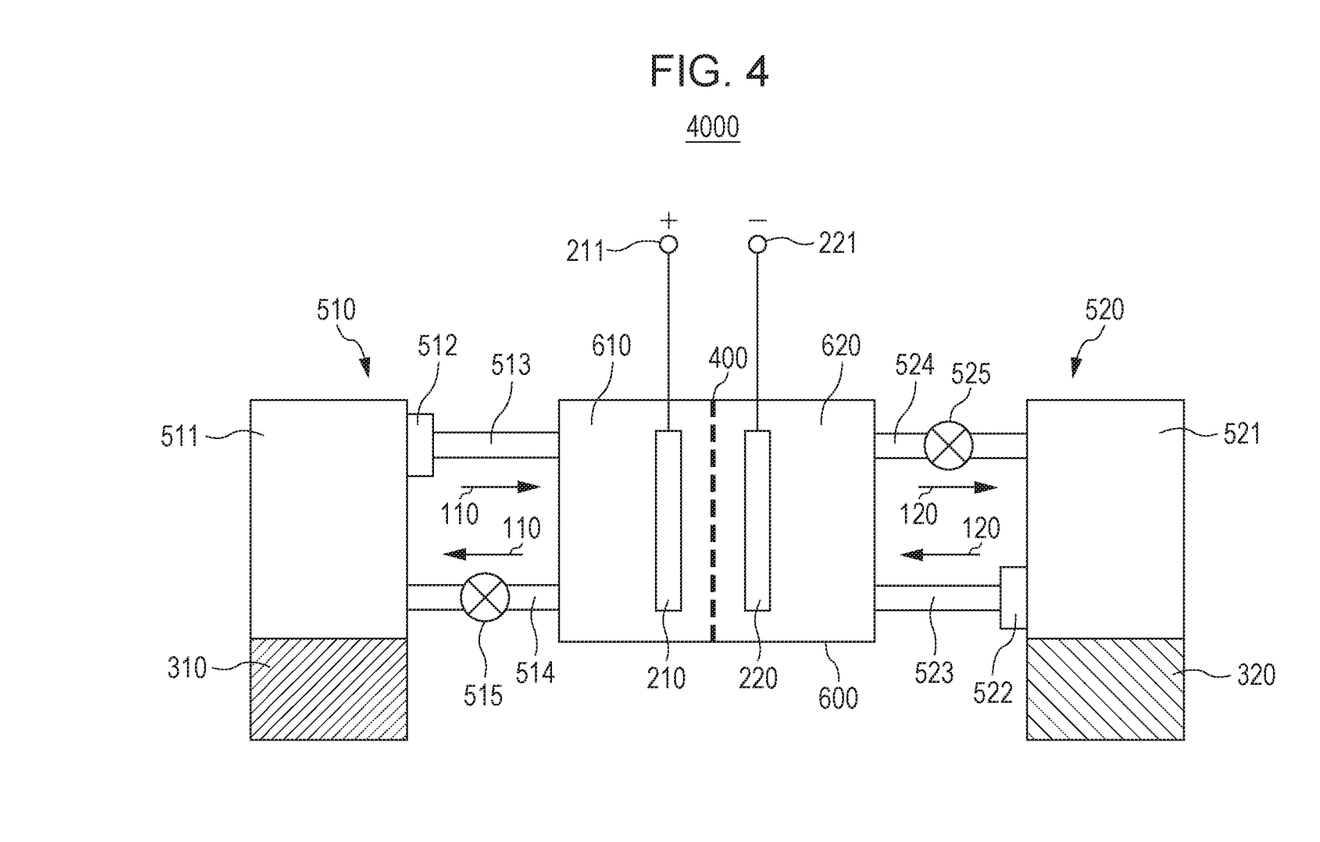
FIG. 4 is a schematic view of a flow battery according to a fourth embodiment.

FIG. 4 is a schematic view of a flow battery 4000 according to the fourth embodiment.

In addition to the components of the flow battery 3000 according to the third embodiment, the flow battery 4000 according to the fourth embodiment further includes the following components.

The flow battery 4000 according to the fourth embodiment includes the first circulation mechanism 510 described in the second embodiment.

The flow battery 4000 according to the fourth embodiment further includes the electrochemical reaction unit 600, the positive-electrode terminal 211, and the negative-electrode terminal 221 described in the second embodiment.

The flow battery 4000 according to the fourth embodiment further includes the second circulation mechanism 520.

The second circulation mechanism 520 includes a second container 521.

The second active material 320 and the second liquid 120 are contained in the second container 521.

The second circulation mechanism 520 circulates the second liquid 120 between the second electrode 220 and the second container 521.

In the second container 521, contact between the second active material 320 and the second liquid 120 causes at least one of an oxidation reaction of the charge mediator 121 with the second active material 320 and a reduction reaction of the discharge mediator 122 with the second active material 320.

In such a structure, the second liquid 120 can come into contact with the second active material 320 in the second container 521. This can increase the contact area between the second liquid 120 and the second active material 320, for example. This can also increase the contact time between the second liquid 120 and the second active material 320. This can efficiently promote an oxidation reaction of the charge mediator 121 with the second active material 320 and a reduction reaction of the discharge mediator 122 with the second active material 320.

In the fourth embodiment, the second container 521 may be a tank.

The second container 521 may contain the second liquid 120, which contains the charge mediator 121 and the discharge mediator 122 dissolved therein, in voids of the second active material 320.

As illustrated in FIG. 4, in the flow battery 4000 according to the fourth embodiment, the second circulation mechanism 520 may include a pipe 523, a pipe 524, and a pump 525.

One end of the pipe 524 is coupled to the positive-electrode chamber 610 or the negative-electrode chamber 620 in which the second electrode 220 is to be disposed. In FIG. 4, one end of the pipe 524 is coupled to the negative-electrode chamber 620.

The other end of the pipe 524 is coupled to an inlet of the second container 521 for the second liquid 120.

One end of the pipe 523 is coupled to an outlet of the second container 521 for the second liquid 120.

The other end of the pipe 523 is coupled to the positive-electrode chamber 610 or the negative-electrode chamber 620 in which the second electrode 220 is to be disposed. In FIG. 4, the other end of the pipe 523 is coupled to the negative-electrode chamber 620.

The pump 525 is disposed on the pipe 524, for example. The pump 525 may be disposed on the pipe 523.

In the flow battery 4000 according to the fourth embodiment, the second circulation mechanism 520 may include a second transfer prevention unit 522.

The second transfer prevention unit 522 prevents the transfer of the second active material 320.

The second transfer prevention unit 522 is disposed on the path through which the second liquid 120 flows from the second container 521 to the second electrode 220. In FIG. 4, the second transfer prevention unit 522 is disposed on the pipe 523.

Such a structure can prevent the second active material 320 from flowing out of the second container 521 (for example, to the second electrode 220). Thus, the second active material 320 remains in the second container 521. Thus, the second active material 320 does not circulate in the flow battery. This can prevent clogging of a component in the second circulation mechanism 520 with the second active material 320. This can also prevent resistive loss due to the second active material 320 flowing to the second electrode 220. The component in the second circulation mechanism 520 is a pipe, for example.

The second transfer prevention unit 522 may be disposed on the joint between the second container 521 and the pipe 523.

For example, the second transfer prevention unit 522 is a filter that filters out the second active material 320. The filter may have openings smaller than the smallest particles of the second active material 320. The filter may be formed of a material that does not react with the second active material 320 and the second liquid 120. The filter may be a glass fiber filter paper, polypropylene nonwoven fabric, polyethylene nonwoven fabric, or a metal mesh that does not react with metallic lithium.

Such a structure can prevent the second active material 320 from flowing out of the second container 521 even when the flow of the second liquid 120 causes the flow of the second active material 320 in the second container 521.

In FIG. 4, the second liquid 120 in the second container 521 is supplied to the negative-electrode chamber 620 through the second transfer prevention unit 522 and through the pipe 523.

Thus, the charge mediator 121 and the discharge mediator 122 dissolved in the second liquid 120 are oxidized or reduced on the second electrode 220.

Subsequently, the second liquid 120 containing the oxidized or reduced charge mediator 121 and discharge mediator 122 dissolved therein is supplied to the second container 521 through the pipe 524 and through the pump 525.

Thus, the charge mediator 121 and the discharge mediator 122 dissolved in the second liquid 120 cause at least one of an oxidation reaction of the charge mediator 121 with the second active material 320 and a reduction reaction of the discharge mediator 122 with the second active material 320.

The circulation of the second liquid 120 may be controlled with the pump 525. More specifically, the supply of the second liquid 120 may be started or stopped with the pump 525, or the amount of the second liquid 120 may be controlled with the pump 525.

The circulation of the second liquid 120 may be controlled by another means other than the pump 525. Another means is a valve, for example.

In FIG. 4, by way of example, the first electrode 210 is a positive electrode, and the second electrode 220 is a negative electrode.

If the first electrode 210 has a relatively low electric potential, the second electrode 220 may function as a positive electrode.

Thus, the second electrode 220 may be a positive electrode, and the first electrode 210 may be a negative electrode.

A heteranthrene compound according to the present disclosure can be used to provide a flow battery with a higher discharge potential and energy density than known flow batteries containing a tetrathiafulvalene derivative as a mediator and LiFePO$_4$ as a solid positive-electrode active material.

The constituents described in the first to forth embodiments may be appropriately combined.

A flow battery according to the present disclosure can be suitable for charge storage devices and charge storage systems, for example.

What is claimed is:

1. A flow battery comprising:
  a first liquid containing a redox mediator;
  a first electrode, wherein the first electrode is a positive electrode;
  a first active material, wherein the first active material is a solid active material that is insoluble in the first liquid and that can occlude and release lithium ions, and wherein the first active material is a lithium-containing transition metal compound; and
  a first circulator that circulates the first liquid between the first electrode and the first active material,
  wherein the redox mediator contains a heteranthrene compound, wherein the heteranthrene compound is a mediator that mediates charge,
  the heteranthrene compound that has a skeletal structure including a central ring structure, the central ring structure containing no nitrogen,
  the first liquid further contains a first electrode side discharge mediator,
  the heteranthrene compound has an oxidation potential,
  the first active material has an equilibrium potential lower than the oxidation potential of the heteranthrene compound, and
  the first active material has a higher equilibrium potential than the first electrode side discharge mediator.

2. The flow battery according to claim 1, wherein the heteranthrene compound is represented by the following general formula (1):

where $X_1$ and $X_2$ each independently denote at least one chalcogen element selected from the group consisting of S, O, Se, and Te, $Y_1$ to $Y_8$ each independently denote hydrogen, fluorine, chlorine, bromine, a cyano group, a nitro group, a chain saturated hydrocarbon group, a chain unsaturated hydrocarbon group, a cyclic saturated hydrocarbon group, a cyclic unsaturated hydrocarbon group, —COR$_1$, or —N(R$_2$)$_2$, $R_1$ and $R_2$ each independently denote at least one selected from the group consisting of hydrogen, a chain saturated hydrocarbon group, a chain unsaturated hydrocarbon group, a cyclic saturated hydrocarbon group, a cyclic unsaturated hydrocarbon group, a cyano group, a nitro group, and any combination thereof, and the chain saturated hydrocarbon group, the chain unsaturated hydrocarbon group, the cyclic saturated hydrocarbon group, and the cyclic unsaturated hydrocarbon group of any of $Y_1$ to $Y_8$ and $R_1$ and $R_2$ may each independently contain at least one selected from the group consisting of oxygen, nitrogen, sulfur, and silicon.

3. The flow battery according to claim 1, wherein the heteranthrene compound is represented by the following general formula (2):

wherein $X_1$ and $X_2$ each independently denote at least one chalcogen element selected from the group consisting of S, O, Se, and Te.

4. The flow battery according to claim 1, wherein the heteranthrene compound is at least one selected from the group consisting of thianthrene, phenoxathiin, and dibenzo[b,e][1,4]dioxin.

5. The flow battery according to claim 1, wherein
the heteranthrene compound has a first redox potential and a second redox potential, and
the first active material has an equilibrium potential higher than the first redox potential and lower than the second redox potential.

6. The flow battery according to claim 1, wherein
the first circulator includes a first container,
the first active material and the first liquid are contained in the first container,
the first circulator circulates the first liquid between the first electrode and the first container, and
contact between the first active material and the first liquid in the first container causes an oxidation reaction and/or a reduction reaction between the first active material and the redox mediator.

7. The flow battery according to claim 6, wherein
the first circulator includes a first transfer prevention filter that prevents transfer of the first active material, and
the first transfer prevention filter is disposed on a path through which the first liquid flows from the first container to the first electrode.

8. The flow battery according to claim 1, further comprising:
a second liquid containing a charge mediator and a discharge mediator;
a second electrode immersed in the second liquid;
a second active material immersed in the second liquid; and
a separator that separates the first electrode and the first liquid from the second electrode and the second liquid,
wherein the charge mediator has a lower equilibrium potential than the second active material, and
the discharge mediator has a higher equilibrium potential than the second active material.

9. The flow battery according to claim 8, wherein
the second liquid contains lithium dissolved therein,
the second active material occludes and releases the lithium,
during charging, the charge mediator is reduced on the second electrode, the charge mediator reduced on the second electrode is oxidized by the second active material, and the second active material occludes the lithium, and
during discharging, the second active material that has occluded the lithium reduces the discharge mediator, the second active material releases the lithium, and the discharge mediator reduced by the second active material is oxidized on the second electrode.

10. The flow battery according to claim 9, wherein
during the charging, the discharge mediator is reduced on the second electrode, and
during the discharging, the charge mediator is oxidized on the second electrode.

11. The flow battery according to claim 8, wherein
the charge mediator and the discharge mediator are fused aromatic compounds, and
the second liquid containing the fused aromatic compounds dissolved therein causes a solvated electron of lithium to be released to dissolve the lithium as a cation.

12. The flow battery according to claim 8, wherein the charge mediator is at least one selected from the group consisting of phenanthrene, biphenyl, o-terphenyl, triphenylene, and anthracene.

13. The flow battery according to claim 8, wherein the discharge mediator is at least one selected from the group consisting of phenanthroline, 2,2'-bipyridyl, benzophenone, trans-stilbene, 4,4'-bipyridyl, 3,3'-bipyridyl, 2,4'-bipyridyl, 2,3'-bipyridyl, cis-stilbene, acetophenone, propiophenone, butyrophenone, valerophenone, and ethylenediamine.

14. The flow battery according to claim 8, further comprising:
a second circulator including a second container,
wherein the second active material and the second liquid are contained in the second container,
the second circulator circulates the second liquid between the second electrode and the second container, and
contact between the second active material and the second liquid in the second container causes an oxidation reaction of the charge mediator with the second active material and/or a reduction reaction of the discharge mediator with the second active material.

15. The flow battery according to claim 14, wherein
the second circulator includes a second transfer prevention filter that prevents transfer of the second active material, and
the second transfer prevention filter is disposed on a path through which the second liquid flows from the second container to the second electrode.

16. The flow battery according to claim 1, wherein
the first electrode side discharge mediator is a heteroaromatic compound or a cyclopentadienyl compound.

* * * * *